(12) United States Patent
Singh et al.

(10) Patent No.: US 6,482,438 B1
(45) Date of Patent: Nov. 19, 2002

(54) APPARATUS AND PROCESS FOR PREPARING CRYSTALLINE PARTICLES

(75) Inventors: Hardev Singh, Dartford; Andrew Theophilus; Robert William Lancaster, both of Stevenage, all of (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/348,948

(22) Filed: Jul. 7, 1999

(30) Foreign Application Priority Data

Dec. 24, 1998 (GB) ............................................. 9828721

(51) Int. Cl.⁷ .......................... A61K 9/14; A61K 9/127; C07C 51/42
(52) U.S. Cl. ........................ 424/489; 424/450; 562/593
(58) Field of Search ................................ 424/489, 450; 562/593, 530; 560/179; 514/2, 21; 530/412

(56) References Cited

U.S. PATENT DOCUMENTS

| | | | |
|---|---|---|---|
| 3,979,269 A | | 9/1976 | Vassilev |
| 5,471,001 A | * | 11/1995 | Anderson et al. ............ 562/593 |
| 5,770,559 A | | 6/1998 | Manning |

FOREIGN PATENT DOCUMENTS

| | | | |
|---|---|---|---|
| DE | 286566 A | | 1/1991 |
| EP | 0619139 A1 | | 3/1994 |
| GB | 627043 | * | 7/1949 |
| GB | 2241783 A | | 9/1991 |
| JP | 2164712 A | | 6/1990 |
| JP | 04097908 A | | 3/1992 |
| RO | 112856 B | | 1/1998 |
| SU | 174521 A | | 7/1992 |
| WO | 97/01509 | | 1/1997 |
| WO | 98/23350 | | 6/1998 |
| WO | WO 00/32591 | | 6/2000 |
| WO | WO 00/32597 | | 6/2000 |
| WO | 00/44468 | | 8/2000 |

OTHER PUBLICATIONS

Shafi, K.V.P.M., Gedanken, A. and Prozorov, "Sonochemical preparation and characterization of nanosized amorphous Co–Ni alloy powders," R. J., Mater.Chem. 1998, 8(3), pp. 769–773.

Quian, Zhao, et. al., "Study on a new process for preparing crystal nuclei of lincomycin hydrochloride," Zhongguo Kangshengsu Zazhi, 22(2), p. 129, 1997.

Kelly, D.R., et. al., "Rapid Crystallisation Using Ultrasonic Irradiation—Sonocrystallisation," Tetrahedron Letters 34(16), pp. 2689–2690, 1993.

Kinzhalov, A.A., et. al., "Kinetics of calcium sulfate crystallization on seeds treated in an ultrasound field," Zh. Prihl. Khim (Leningrad), 43(11) pp. 2402–2406, 1970.

Ladinskaya, S.I., et. al., "Effect of ultrasonic vibrations on the crystallization of phytosterol from alcohol solutions of its sulfate soap," Nauch Tr., Leningrad. Lesotekh. Akad. No. 114, pp. 57–67, 1969.

Gatumel, C., et al., "Nucleation Control in Prescipitation Processes by Ultrasound," Kona Powder and Particle, No. 16 pp. 160–168, 1998.

Martin, Peter, et. al., "Sonochemistry," Process Technology, pp. 6–9, 1997.

(List continued on next page.)

Primary Examiner—Thurman K. Page
Assistant Examiner—Blessing Fubara
(74) Attorney, Agent, or Firm—James P. Riek

(57) ABSTRACT

There is provided according to the present invention a process for preparing crystalline particles, especially particles of a pharmaceutical or carrier substance suitable for inhalation therapy, in addition to apparatus for the preparation of such particles.

18 Claims, 13 Drawing Sheets

OTHER PUBLICATIONS

Cains, Peter W., et. al., "The Use of Ultrasound in Industrial Chemical Synthesis and Crystallization. 1. Applications to Synthetic Chemistry," *Organic Process Research & Development* 2, pp. 34–48, 1998.

Copy of slides used in a presentation at UK Atomic Energy Authority (AEA) in a meeting of Mar. 3, 1998.

Handout from UK Atomic Energy Authority (AEA) subsequent to a meeting of Mar. 1998.

Gatumel et al., "Nucleation Control in Precipitation Processes by Ultrasound," 1998, pp. 160–168.*

J. Berlan, et. al., "Sonochemistry: from research laboratories to industrial plants," *Ultrasonics* 1992, vol. 30, No. 4, pp. 203–212.

P. D. Martin, et. al., "Reactor Design for Sonochemical Engineering," *Trans IchemE*, vol 70, Part A, May 1992, pp. 296–303.

T. J. Mason, "Industrial sonochemistry: potential and practicality," *Ultrasonics* 1992, vol 30, No. 3, pp. 192–196.

Otakar Sohnel and John Garside, "Precipitation: Basic Principles & Industrial Applications," book published by Butterworth–Heinemann, Ltd., 1992, Chapter 5, Section 5.1.3 and Chapter 7, Section 7.2.1.

* cited by examiner

| High Under Size % | High Under Size % | High Under Size % | High Under Size % | High Under Size % | High Under Size % | Span 2.86 |
|---|---|---|---|---|---|---|
| 80.0 100 | 24.9 98.3 | 7.75 79.9 | 2.41 32.6 | 0.75 6.9 | 0.23 0.6 | D[4,3] 5.45μm |
| 71.9 100 | 22.4 97.8 | 6.97 76.3 | 2.17 28.8 | 0.68 5.8 | 0.21 0.4 | |
| 64.7 99.9 | 20.1 97.2 | 6.27 72.5 | 1.95 25.3 | 0.61 4.8 | 0.19 0.3 | D[3,2] 2.08μm |
| 58.2 99.9 | 18.1 96.4 | 5.64 68.4 | 1.75 22.1 | 0.55 4.0 | 0.17 0.2 | |
| 52.3 99.8 | 16.3 95.3 | 5.07 64.1 | 1.58 19.2 | 0.49 3.2 | 0.15 0.1 | D[v,0.9] 11.47μm |
| 47.1 99.7 | 14.6 94.0 | 4.56 59.5 | 1.42 16.6 | 0.44 2.6 | 0.14 0.1 | |
| 42.3 99.6 | 13.2 92.5 | 4.10 54.9 | 1.28 14.4 | 0.40 2.1 | 0.12 0.1 | D[v,0.1] 0.97μm |
| 38.1 99.4 | 11.8 90.6 | 3.69 50.2 | 1.15 12.5 | 0.36 1.6 | 0.11 0.0 | |
| 34.2 99.3 | 10.7 88.5 | 3.32 45.7 | 1.03 10.9 | 0.32 1.3 | 0.10 0.0 | D[v,0.5] 3.67μm |
| 30.8 99.0 | 9.58 85.9 | 2.98 41.2 | 0.93 9.4 | 0.29 1.0 | | |
| 27.7 98.7 | 8.62 83.1 | 2.68 36.8 | 0.83 8.1 | 0.26 0.7 | | Shape OFF |

Source = Data:19aug98　　Beam length = 2.4 mm　Model indp
Record No. = 11　　　　　Residual = 0.378 %
Focal length = 45 mm　　Obscuration = 0.1470　Volume Conc. = 0.0059%
Presentation = 0607　　　Volume distribution　Sp.S.A 2.8848 m²/cc.

Figure 1:
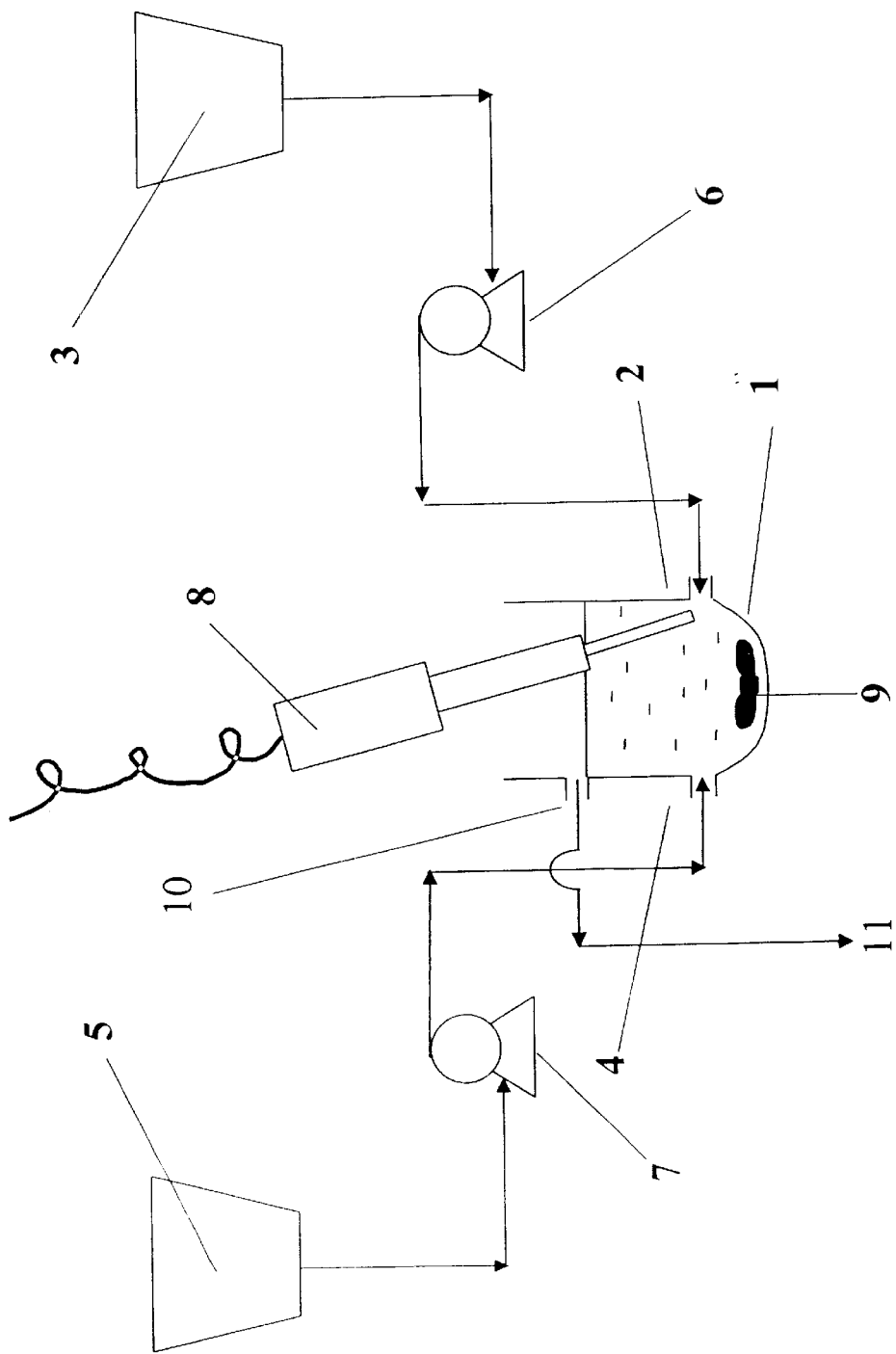
Figure 2:
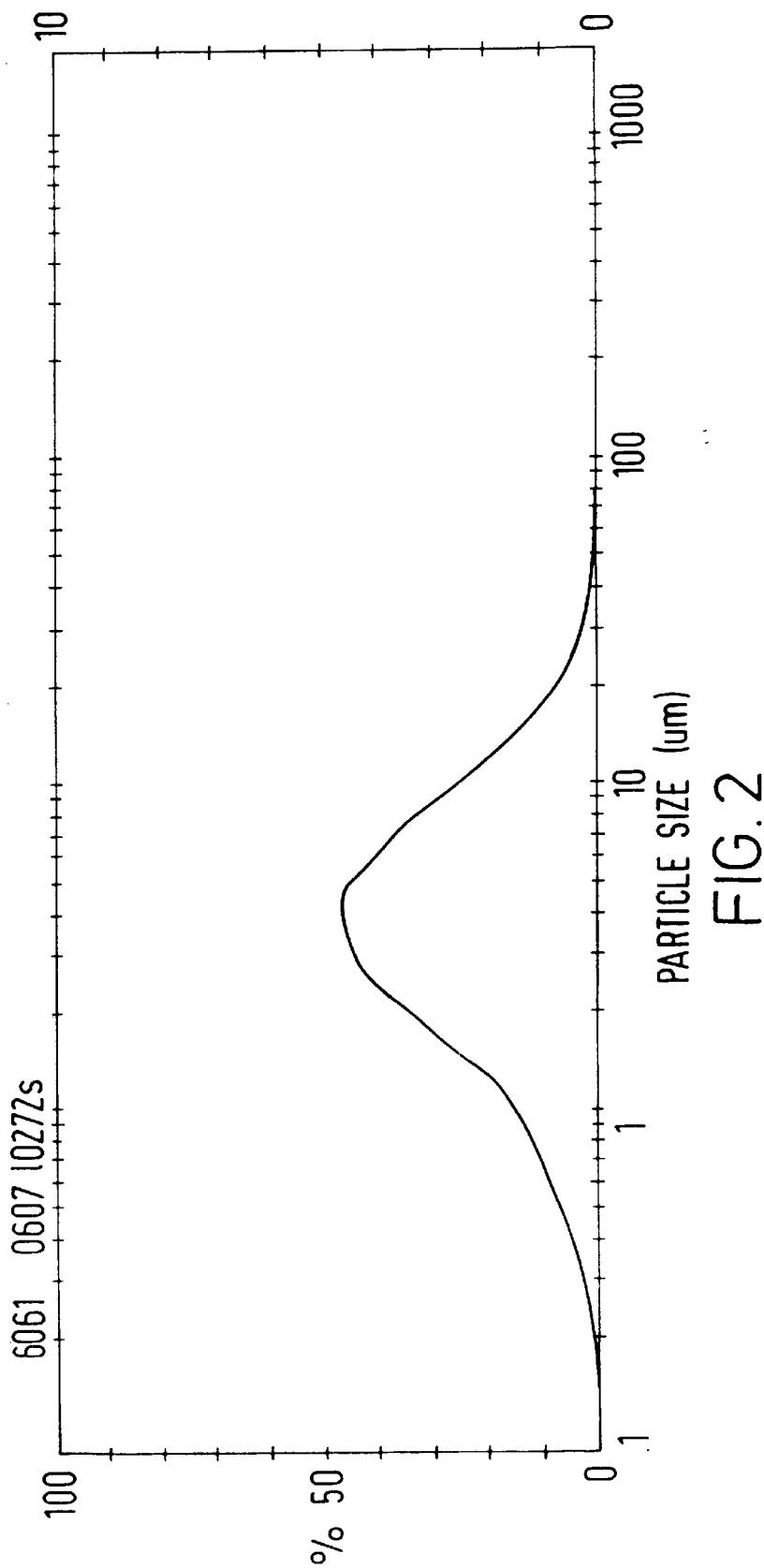

MALVERN INSTRUMENTS
FIG. 2 cont.

FIG. 7 cont.

| Size (um) | Volume In % | Size (um) | Volume In % | Size (um) | Volume In % | Size (um) | Volume In % |
|---|---|---|---|---|---|---|---|
| 0.055 | 0.01 | 0.700 | 0.13 | 8.06 | 2.93 | 92.79 | 0.00 |
| 0.061 | 0.05 | 0.772 | 0.19 | 8.89 | 2.48 | 100.00 | 0.00 |
| 0.074 | 0.05 | 0.851 | 0.27 | 9.80 | 0.46 | 112.8 | 0.00 |
| 0.082 | 0.06 | 0.938 | 0.23 | 10.00 | 3.33 | 124.4 | 0.00 |
| 0.090 | 0.09 | 1.00 | 0.64 | 11.91 | 1.42 | 150.0 | 0.00 |
| 0.100 | 0.10 | 1.14 | 0.72 | 13.14 | 1.15 | 151.3 | 0.00 |
| 0.109 | 0.14 | 1.26 | 0.98 | 14.49 | 0.93 | 166.8 | 0.00 |
| 0.120 | 0.19 | 1.39 | 1.29 | 15.97 | 0.77 | 183.9 | 0.00 |
| 0.133 | 0.25 | 1.53 | 1.75 | 17.62 | 0.79 | 200.0 | 0.00 |
| 0.147 | 0.31 | 1.69 | 2.11 | 20.00 | 0.35 | 223.6 | 0.00 |
| 0.162 | 0.39 | 1.86 | 1.91 | 21.42 | 0.43 | 250.0 | 0.00 |
| 0.178 | 0.65 | 2.00 | 3.87 | 23.62 | 0.36 | 271.9 | 0.00 |
| 0.200 | 0.58 | 2.26 | 3.63 | 26.04 | 0.29 | 300.0 | 0.00 |
| 0.217 | 0.82 | 2.49 | 4.16 | 28.72 | 0.11 | 330.6 | 0.00 |
| 0.239 | 0.95 | 2.75 | 4.40 | 30.00 | 0.31 | 364.6 | 0.00 |
| 0.263 | 1.41 | 3.03 | 4.66 | 34.92 | 0.12 | 400.0 | 0.00 |
| 0.300 | 0.68 | 3.34 | 4.98 | 38.50 | 0.04 | 443.3 | 0.00 |
| 0.320 | 0.96 | 3.69 | 5.06 | 40.00 | 0.04 | 488.8 | 0.00 |
| 0.353 | 0.84 | 4.07 | 5.00 | 42.45 | 0.02 | 500.0 | 0.00 |
| 0.389 | 0.22 | 4.48 | 5.73 | 50.00 | 0.00 | 600.0 | 0.00 |
| 0.400 | 1.15 | 5.00 | 4.43 | 56.92 | 0.00 | 651.4 | 0.00 |
| 0.474 | 0.30 | 5.45 | 4.72 | 62.76 | 0.00 | 655.4 | 0.00 |
| 0.500 | 0.62 | 6.01 | 4.30 | 69.21 | 0.00 | 700.0 | 0.00 |
| 0.576 | 0.13 | 6.63 | 3.84 | 76.32 | 0.00 | 800.0 | 0.00 |
| 0.600 | 0.32 | 7.31 | 3.38 | 84.15 | 0.00 | 850.0 | 0.00 |
| 0.700 | | 8.06 | | 92.79 | 0.00 | 878.7 | 0.00 |

| Size (um) | Volume In % | Size (um) | Volume In % | Size (um) | Volume In % | Size (um) | Volume In % |
|---|---|---|---|---|---|---|---|
| 0.055 | 0.04 | 0.700 | 0.20 | 8.06 | 2.31 | 92.79 | 0.01 |
| 0.061 | 0.14 | 0.772 | 0.23 | 8.89 | 1.77 | 100.00 | 0.01 |
| 0.074 | 0.12 | 0.851 | 0.29 | 9.80 | 0.31 | 112.8 | 0.01 |
| 0.082 | 0.13 | 0.938 | 0.22 | 10.00 | 1.91 | 124.4 | 0.01 |
| 0.090 | 0.19 | 1.00 | 0.61 | 11.91 | 0.61 | 150.0 | 0.00 |
| 0.100 | 0.20 | 1.14 | 0.68 | 13.14 | 0.38 | 151.3 | 0.00 |
| 0.109 | 0.27 | 1.26 | 0.93 | 14.49 | 0.23 | 166.8 | 0.00 |
| 0.120 | 0.37 | 1.39 | 1.23 | 15.97 | 0.14 | 183.9 | 0.00 |
| 0.133 | 0.45 | 1.53 | 1.68 | 17.62 | 0.15 | 200.0 | 0.00 |
| 0.147 | 0.55 | 1.69 | 2.05 | 20.00 | 0.10 | 223.6 | 0.00 |
| 0.162 | 0.67 | 1.86 | 1.88 | 21.42 | 0.18 | 250.0 | 0.00 |
| 0.178 | 1.07 | 2.00 | 3.83 | 23.62 | 0.20 | 271.9 | 0.00 |
| 0.200 | 0.92 | 2.26 | 3.62 | 26.04 | 0.23 | 300.0 | 0.00 |
| 0.217 | 1.29 | 2.49 | 4.19 | 28.72 | 0.11 | 330.6 | 0.00 |
| 0.239 | 1.46 | 2.75 | 4.47 | 30.00 | 0.37 | 364.6 | 0.00 |
| 0.263 | 2.14 | 3.03 | 4.78 | 34.92 | 0.22 | 400.0 | 0.00 |
| 0.300 | 1.03 | 3.34 | 5.13 | 38.50 | 0.08 | 443.3 | 0.00 |
| 0.320 | 1.46 | 3.69 | 5.25 | 40.00 | 0.11 | 488.8 | 0.00 |
| 0.353 | 1.28 | 4.07 | 5.34 | 42.45 | 0.24 | 500.0 | 0.00 |
| 0.389 | 0.34 | 4.48 | 6.04 | 50.00 | 0.12 | 600.0 | 0.00 |
| 0.400 | 1.79 | 5.00 | 4.39 | 56.92 | 0.06 | 651.4 | 0.00 |
| 0.474 | 0.47 | 5.45 | 4.55 | 62.76 | 0.04 | 655.4 | 0.00 |
| 0.500 | 0.98 | 6.01 | 4.05 | 69.21 | 0.02 | 700.0 | 0.00 |
| 0.576 | 0.21 | 6.63 | 3.45 | 76.32 | 0.01 | 800.0 | 0.00 |
| 0.600 | 0.54 | 7.31 | 2.87 | 84.15 | 0.01 | 850.0 | 0.00 |
| 0.700 |  | 8.06 |  | 92.79 | 0.01 | 878.7 | 0.00 |

FIG. 8 cont.

APPARATUS AND PROCESS FOR PREPARING CRYSTALLINE PARTICLES

This application claims priority to GB9828721.2 filed Dec. 24, 1998.

This invention relates to a novel apparatus for preparing crystalline particles, particularly particles of defined particle size distribution, especially particles of therapeutically useful or carrier substances of a size suitable for inhalation therapy. There is also provided a process for preparing the same.

Industrial processes for production of many products, particularly pharmaceutical products, require the preparation of pure substances of a defined particle size distribution. Pure substances are frequently prepared by precipitation from solutions of lesser purity. When precipitation takes place relatively slowly (eg over a matter of hours), crystals are grown which are frequently of an non-uniform shape and relatively large size.

In the field of inhalation therapy, therapeutic molecules are generally desired of a particle size "suitable for inhalation", which is a term generally taken to indicate an aerodynamic diameter between 1 and 10 $\mu$m, especially 1 and 5 $\mu$m, particularly 1 and 3 $\mu$m. Carrier molecules (such as lactose) for inhaled therapeutic preparations are typically desired of a significantly larger aerodynamic diameter so that they do not penetrate into the upper respiratory tract to the same degree as the active ingredient and an aerodynamic diameter of 100 to 150 $\mu$m is generally considered suitable. However this is a generalisation and for some purposes it may well be preferred to use a lower particle size for the carrier, even one comparable to that of the therapeutic substance.

Particles of the desired particle size for inhalation therapy are conventionally prepared by milling or micronisation. These processes, depending on the precise conditions adopted, are capable of generating particles distributions which include fractions having particles with the appropriate size. Milling is suitable for preparing particles of the larger size indicated above and micronisation of the smaller size indicated above. However, there are a number of disadvantages associated with milling and micronisation processes including that the fraction having the desired particle size may be relatively small, that there may be generated a significant fraction of particles that are finer than is desired (which may be deleterious eg if it affects bioavailability) and that product losses generally may be considerable. A further property of micronised products is that the surfaces of the particles generated are generally substantially amorphous (i.e. have minimal crystallinity). This may be undesirable when there exists a tendency for the amorphous regions to convert to a more stable crystalline state.

Rapid precipitation (eg by dilution of a solution with an anti-solvent) may give rise to crystalline particles which could be of suitable size, however this technique is notoriously difficult to control and has not found widespread acceptance in the pharmaceutical industry, particularly in relation to inhalation products.

The use of ultrasonic radiation to increase effectiveness of crystallisation in purification of organic substances is described in Yurhevich, et al. (1972), Primen. Ul'trazvuka Met. Protsessakh, Mosk. Inst. Stali Splavov 67, 103–106.

We have now invented a novel process and apparatus for preparing particles which overcomes or substantially mitigates one or more of the above mentioned disadvantages.

Thus according to a first aspect of the invention there is provided a process for preparing crystalline particles of substance which comprises mixing in a continuous flow cell in the presence of ultrasonic radiation a flowing solution of the substance in a liquid solvent with a flowing liquid antisolvent for said substance which is miscible with the liquid, and collecting the resultant crystalline particles generated.

A particular advantage of the process is that is capable of running continuously (subject to adequate supply of solution and anti-solvent) even if, for a particular application, it may be desired to run it only for a relatively short time.

A feature of the process is that in a steady state the concentration of dissolved substance in the mixing chamber of the flow cell remains approximately constant since the precipitating substance is replaced by the inflow of further solution. This allows the process to be run continuously and reproducibly.

According to a second aspect of the invention there is provided an apparatus for preparing crystalline particles of a substance which comprises (i) a first reservoir of said substance dissolved in a liquid solvent;
(ii) a second reservoir of liquid antisolvent for said substance which is miscible with the liquid solvent;
(iii) a mixing chamber having first and second inlet ports and an outlet port;
(iv) means for delivering the contents of the first and second reservoirs to the mixing chamber via the first and second inlet ports respectively at independent controlled flow rate;
(v) a source of ultrasonic radiation located in the vicinity of the first inlet; and
(vi) means for collecting crystalline particles suspended in the liquid discharged from the mixing chamber at the outlet port.

Preferably the apparatus further comprises means to mix the liquids delivered to the mixing chamber via the first and second inlets. The preferred means is a stirrer. Most preferably the mixing means should be non grinding eg a non-grinding magnetic stirrer or an overhead stirrer (particularly a non-grinding magnetic stirrer).

Desirably, stirring speed will be set a level that gives efficient mixing in the mixing chamber, but without inducing vortex effects. Vortex effects are undesirably since they have a tendency to disrupt the cavitation caused by the source of ultrasonic radiation. Furthermore they may cause particle size reduction through liquid micronisation-like processes.

Desirably the means for delivering the contents of the first and second reservoirs to the mixing chamber via the first and second inlet ports respectively at independent controlled flow rate comprises one or more pumps. Preferably a pump will be provided for each of the first and second reservoirs. A range of pumps are available and may be suitable for the apparatus according to the invention. The pump may, for example, be a peristaltic pump. Pumps which are essentially non-pulsing are preferred.

The contents of the first and second reservoirs may be delivered to the mixing chamber at a range of flow rates which will be selected and optimised according to the nature of the substance, the solvent, the antisolvent and the power and frequency of the source of ultrasonic radiation. Typically flow rates will be in the range of 0.5–50 ml/min.

Preferably the outlet port of the apparatus is disposed above the inlet ports in the mixing chamber such that the liquid in the mixing chamber flows from a lower to a higher point in the chamber before exiting. This arrangement optimises mixing and allows ready balance of the rates of inflow and outflow.

Preferably the mixing chamber is substantially circular in section and the first and second inlet ports are disposed diametrically opposite each other and at the same height relative to the base of the mixing chamber. Nevertheless, it may be conceived to orientate the two inlet ports in an off-set manner in order to give some circular motion to the inflowing liquids, although this is not generally preferred.

The position of the outlet port relative to the inlet ports is believed to have an influence on the size of the crystalline particles generated. Without being limited by theory, it is believed that the greater the distance between the inlet ports and outlet port, the greater the average residence time if the particles in the flow cell, the longer the crystalline particles have to mature and hence the larger the mean particle size. However it will be appreciated that mean particle size is subject to a number of other influences.

Preferably the exit port is located approximately half way up the side of the mixing chamber.

In one particular embodiment of the invention, the apparatus according to the invention is provided with a number of optional outlet points at different heights relative to the inlet port. Fractions of differing particles size may then be "tapped" from the different outlet ports.

The mixing chamber may be manufactured from a range of conventional materials however these will preferably be selected so as to be unreactive with the substance, the solvent or the anti-solvent. The mixing chamber may be of any suitable size, whether of a size suitable for bench-scale preparation, industrial pilot scale preparation or industrial manufacturing scale.

Particles suspended in the liquid discharged from the mixing chamber at the outlet port may be collected by means of one of a number of conventional particle capturing techniques eg filtration or centrifugation. The preferred means is a filtration means; a wide range of suitable filters are known to persons skilled in the art. The filter may be provided with a drying facility.

Alternatively in a system where the crystallisation of the substance out of solution is essentially complete, the outflow from the mixing chamber may be fed to a spray-drying facility such that the solvent/antisolvent mixture is vaporised and the particles collected dry.

Ultrasound frequencies above around 20 kHz are generally suitable; frequencies in the range 20–25 kHz are particularly suitable, especially 22 kHz. Lower frequencies than these are generally to be avoided since they may fall within a range audible to the human ear. For a given geometry of mixing chamber, certain frequencies may be prone to cancellation. Generally this phenomenon may be avoided by modest tuning of the probe frequency.

Ultrasound power in the range 5–5000 W may be suitable (although we are not aware of any theoretical upper limit); in general smaller particles are obtainable using higher power.

The source of ultrasonic radiation will be located sufficiently close to the first inlet port such that it efficiently aids induction of precipitation of particles of substance by causing cavitation in the mixing liquids. Preferably the source is located just above the first inlet port.

The source of ultrasonic radiation may be enclosed in a protective jacket (eg one made of glass) containing a sono-radiation transmission fluid (eg silicone or olive oil).

As a further aspect of the invention we provide a process for preparing crystalline particles of a substance using an apparatus according to the invention which comprises (i) delivering the contents of the first and second reservoirs to the mixing chamber via the first and second inlet ports respectively at independent controlled flow rate;

(ii) supplying ultrasonic radiation to the vicinity of the first inlet; and (iii) collecting the crystalline particles suspended in the liquid discharged from the mixing chamber at the outlet port.

The process is particularly suitable for preparing particles of substances which are pharmaceutical or carrier substances suitable for inhalation therapy.

Examples of pharmaceutical substances suitable for inhalation therapy include analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone, fluticasone, flunisolide, budesonide, rofleponide, mometasone or triamcinolone; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; and salts, esters and solvates of any of the above.

Pharmaceutical substances of particular interest include fluticasone, beclomethasone, salmeterol, salbutamol or an ester, salt or solvate thereof. The substance of most interest is salmeterol xinafoate. Fluticasone propionate is also of particular interest.

Examples of carrier substances include lactose.

The solvent and antisolvent liquids will be selected so as to be appropriate for the substance. It is also necessary that they are readily miscible in the proportions employed. Suitable combinations of solvent/antisolvent include acetone/water, ethanol/IPA, methanol/IPA, methanol/water, DMF/water, DMAc/water, DMSO/water and reciprocal pairs.

1,1,1,2-tetrafluoroethane (HFA134a) and 1,1,1,2,3,3,3-heptafluoro-n-propane (HFA227) are also potential solvents or antisolvents which may be paired eg with ethanol. However the use of these gases in liquefied form would require the use of cold or pressurised equipment.

For generation of small particles by the process according to the invention, it is preferred that the difference between the dissolution properties of the solvent and anti-solvent be as great as possible. For reasons of industrial efficiency (particularly in order to reduce the throughput volumes of liquid) it is preferred to use concentrations of substance in solvent which are as high as possible. Nevertheless the solutions must be stable and not prone to crystallisation before discharge into the continuous flow cell. With this end in mind, it may be preferred to use the solution of the substance in the solvent at elevated temperature. It may also be preferable to cool the anti-solvent.

In order to prevent premature precipitation of the dissolved substance in the lines it will generally be desired to prime the apparatus by first pumping it with solvent. It may be preferred to prime the apparatus by pumping it with heated solvent, particularly when the dissolved substance is close to its solubility limit.

The optimum relative flow rates of substance/solvent solution and anti-solvent will generally depend on the solubility of the substance in the solvent relative to the anti-solvent. The lower this ratio is, the lower may be the flow rate of anti-solvent relative to the substance/solvent solution.

Higher flow rates of anti-solvent have a tendency to result in crystalline particles of smaller mean size.

When the substance is fluticasone propionate we prefer the solvent to be acetone and the anti-solvent to be water.

When the substance is salmeterol xinafoate we prefer the solvent to be methanol or acetone (more preferably methanol) and the anti-solvent to be water or IMS (more preferably water).

When the substance is salbutamol sulphate, we prefer the solvent to be water and the anti-solvent to be IMS.

When the substance is beclomethasone dipropionate we prefer the solvent to be IMS and the anti-solvent to be water.

When the substance is lactose we prefer the solvent to be water and the anti-solvent to be ethanol.

When the substance is budesonide, we prefer the solvent to be IMS and the anti-solvent to be water.

When the substance is formoterol fumarate or terbutaline sulphate we prefer the solvent to be methanol or acetone and the anti-solvent to be water or IMS.

As a further aspect of the invention we provide a population of particles obtainable by a process according to the invention.

Particles of pharmaceutical or carrier substances may be obtained which are suitable for use in a pharmaceutical composition for inhalation therapy, such as dry powder composition (whether containing pure drug, or drug mixed with a carrier such as lactose) or a pressurised liquid formulation (eg a formulation comprising a hydrofluoroalkane propellant such as HFA134a or HFA227).

Pressurised liquid formulations suitable for metered-dose inhalers will be retained in canisters, typically aluminium canisters (which may be plastics lined) which are provided with a metering valve of appropriate metering volume.

We also provide a pharmaceutical composition comprising a population of particles prepared according to the invention.

The advantages that the invention may possess include the fact that the process may be performed in a continuous manner without requirements for batch processing, that process may be scaled up with relative ease and that the apparatus and process are capable of producing particle size distributions of very high uniformity index.

The invention will be illustrated by reference to FIG. 1 in which mixing chamber 1 is provided with first inlet port 2 connected to first reservoir 3 containing substance dissolved in solvent and second inlet port 4 connected to second reservoir 5 containing anti-solvent. Pumps 6 and 7 deliver liquid from reservoirs 3 and 5 to mixing chamber 1 at a controlled rate. An ultrasound probe 8 is located in the vicinity of, and just above, inlet port 2. When pumps 6 and 7 are in operation, liquids from reservoirs 3 and 5 are delivered to mixing chamber 1 and are mixed with the aid of magnetic stirrer 9. Liquid containing the particles of substance thus generated flows out of the mixing chamber via exit port 10 where they are collected by means of filter 11.

In the mixing chamber used in Examples 1 and 2, the diameter was 5 cm the height was 12.5 cm, the height of the outlet above the base was 7 cm and the height of the inlets above the base was 1.5 cm.

EXAMPLE 1

Distributions of Particles of Crystalline Fluticasone Propionate

Experimental Procedure

A continuous flow reaction cell with 2 diametrically opposite inlets at the bottom and a run-out ca. half way up the side of the vessel is used in the experiment. The drug substance (fluticasone propionate, FP) is dissolved in acetone (15 vol, 0.133 M) at elevated temperature (50–56° C.) and then allowed to cool to ambient temperature (20° C.). A solution of FP is then pumped using a peristaltic pump into one of the bottom inlets of the reaction cell. Water was similarly pumped via the other inlet from a water reservoir using a second pump.

Re-crystallisations are carried out from various mixtures of acetone and water (by altering the flow rates of each) as dictated by the parameters set out in the experimental design. Efficient mixing of the two streams is ensured with the aid of a non-grinding magnetic stirrer bar.

Before carrying out any particular crystallisation, the cell is pre-charged with a mixture of acetone/water (the ratio of each being the same as the relative pumping rates from the two reservoirs). By doing this, the relative concentrations of the water to acetone remains constant throughout the crystallisation. The tip of the sono-probe is arranged so that it is just above the inlet for the FP solution. When the magnetic stirrer, sono-probe and pumps are turned on, rapid onset of crystallisation takes place. A suspension of the crystallisation mixture exits via the overflow directly on to a filter funnel thus minimising the opportunity for further crystal growth.

Using the above set-up, the experiments set out in the experimental design shown below were carried out and the samples of damp solid harvested and dried in vacuo at ambient temperature. All the samples were sized using the Malvern laser diffraction particle sizer and the results analysed using multi-dimensional model fitting software (such as Design Expert 5).

Experimental Design

Ultrasound, stirring rate using the magnetic stirrer, flow rate of the FP acetone solution and flow rate of the water were included as variables in the experimental design. Appropriate maximum and minimum values for each of the four variables were chosen as shown in Table 1.

TABLE 1

| Variable | Units | Minimum Value | Mid Point | Maximum Value |
|---|---|---|---|---|
| A Water antisolvent flow rate | ml/min | 12 | 18 | 24 |
| B Drug acetone solution flow rate | ml/min | 3.5 | 5.25 | 7.0 |
| C Stirring Rate | % | 0 | 20 | 40 |
| D Ultrasound Power | % | 0 | 20 | 40 |

A half factorial design was chosen to model the 4 variable experiment and the software package Design Expert 5 was used to generate the design. Two centrepoints were added to the design bringing the total number of experiments to 10.

Ultrasound Power is given as a percentage of maximum (50 W). Ultrasound frequency was 22 kHz.

Analysis

Samples were analysed using Malvern laser diffraction particle sizing.

Instrument: Malvern Mastersizer X

Lens: 45 mm Reverse Fourier

Analysis: 0607 presentation code

Dispersant: Iso Octane / Lecithin 0.05% w/w

Pre dispersion: Sonicate for 10 seconds

Obscuration: 10% to 16%

One analysis per sample was carried out. The median particle size (D50), particle size at 90% undersize (D90) and particle size at 10% undersize (D10) were used as responses to characterise the medium, course, and fine particles. In addition a fourth response, uniformity index (Ul) was calculated as a measure of the breadth of the distribution.

Results (a) Size Results

TABLE 2

| Run N° | Water ml/min | Acetone ml/min | Stirring % | U/sound % | D50 ($\mu$m) | D10 ($\mu$m) | D90 ($\mu$m) | UI (%) |
|---|---|---|---|---|---|---|---|---|
| 1 | 24 | 3.50 | 40.00 | 0.00 | 4.95 | 1.07 | 18.91 | 5.7 |
| 2 | 18 | 5.25 | 20.00 | 20.00 | 4.56 | 1.02 | 14.29 | 7.1 |
| 3 | 24 | 3.50 | 0.00 | 40.00 | 4.2 | 1 | 18.3 | 5.3 |
| 4 | 12 | 7.00 | 0.00 | 40.00 | 7.52 | 2.62 | 20.83 | 12.6 |
| 5 | 24 | 7.00 | 40.00 | 40.00 | 4.3 | 1.05 | 14.66 | 7.2 |
| 6 | 18 | 5.25 | 20.00 | 20.00 | 5.28 | 0.89 | 17.16 | 5.1 |
| 7 | 12 | 3.50 | 0.00 | 0.00 | 9.34 | 2.32 | 28.97 | 8 |
| 8 | 12 | 7.00 | 40.00 | 0.00 | 3.46 | 1.06 | 9.33 | 11.4 |
| 9 | 12 | 3.50 | 40.00 | 40.00 | 3.67 | 0.97 | 11.47 | 8.5 |
| 10 | 24 | 7.00 | 0.00 | 0.00 | 9.79 | 1.48 | 37.62 | 3.9 |

Uniformity Index (Ul) is calculated as 100×D10/D90.

The particle size distribution for Run 9 is shown graphically in FIG. 2.

(b) Analysis of Effects

Effect graphs to show the interdependence of pairs of variables A, B, C, D were constructed using Design Expert 5 and are shown in FIGS. 3–6.

A− and A+ indicate, respectively, the minimum and maximum values of variable A shown in Table 1. B−/B+, C−/C+ and D−/D+ may be interpreted similarly.

$R^2$ is a measure of closeness of fit; $R^2=1$ being the measure of perfect fit.

Figure 3:
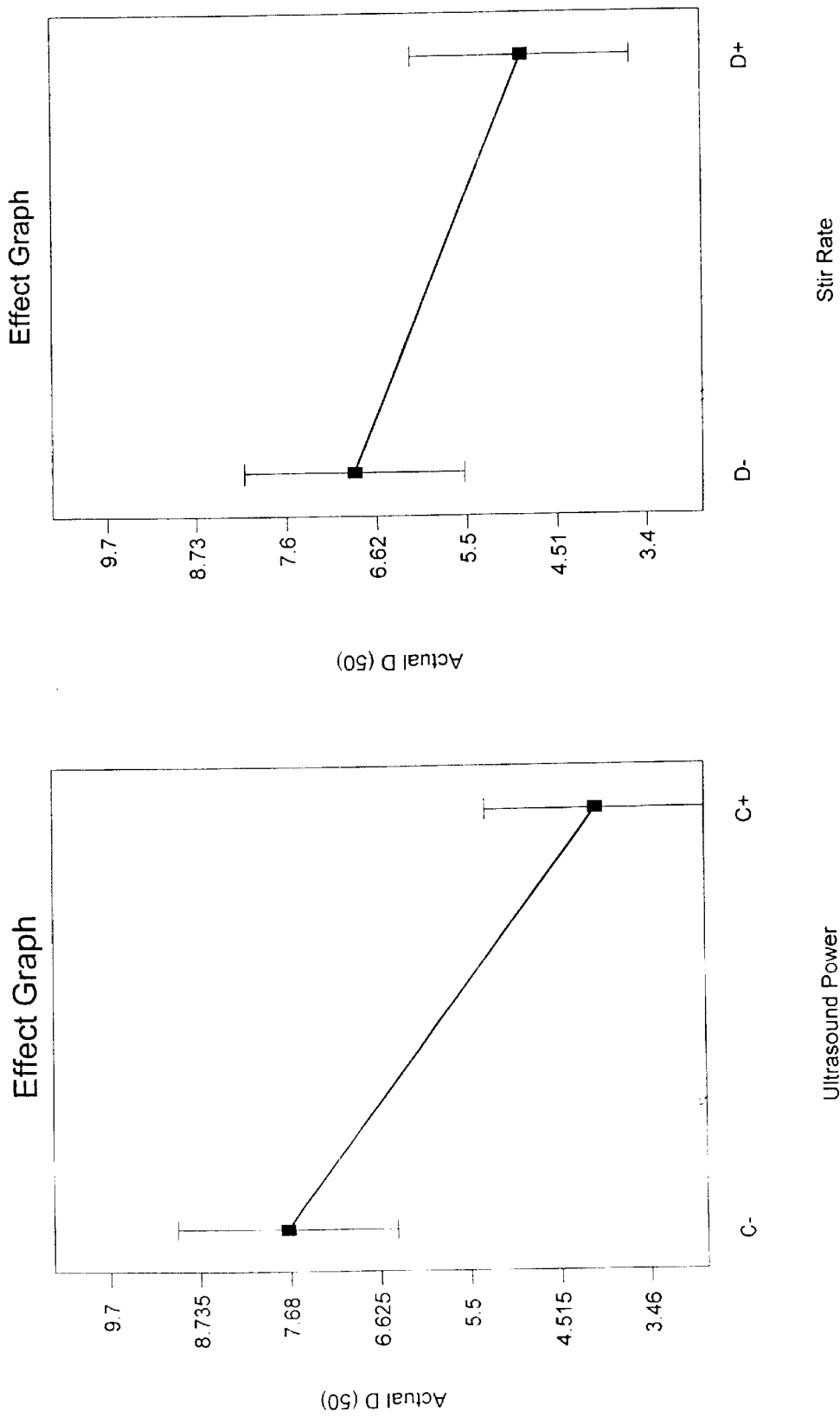

FIG. 3: effect of ultrasound power or stir rate on D50; ultrasound has a major effect and stirring rate has a minor effect ($R^2=0.72$).

Figure 4:
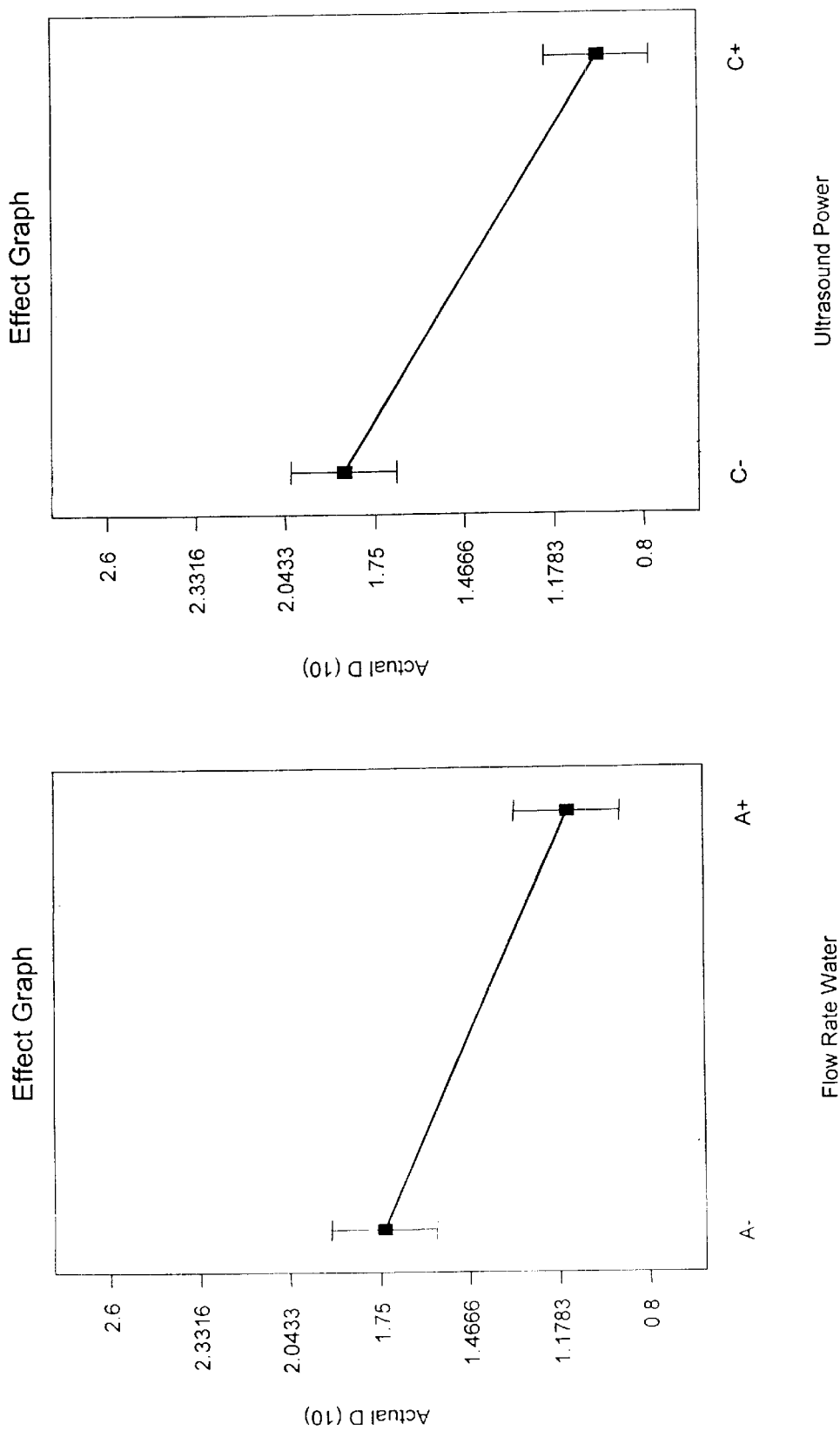

FIG. 4: effect of anti-solvent flow rate or ultrasound power on D10; ultrasound and anti-solvent flow rate both have a major effect ($R^2=0.94$).

Figure 5:
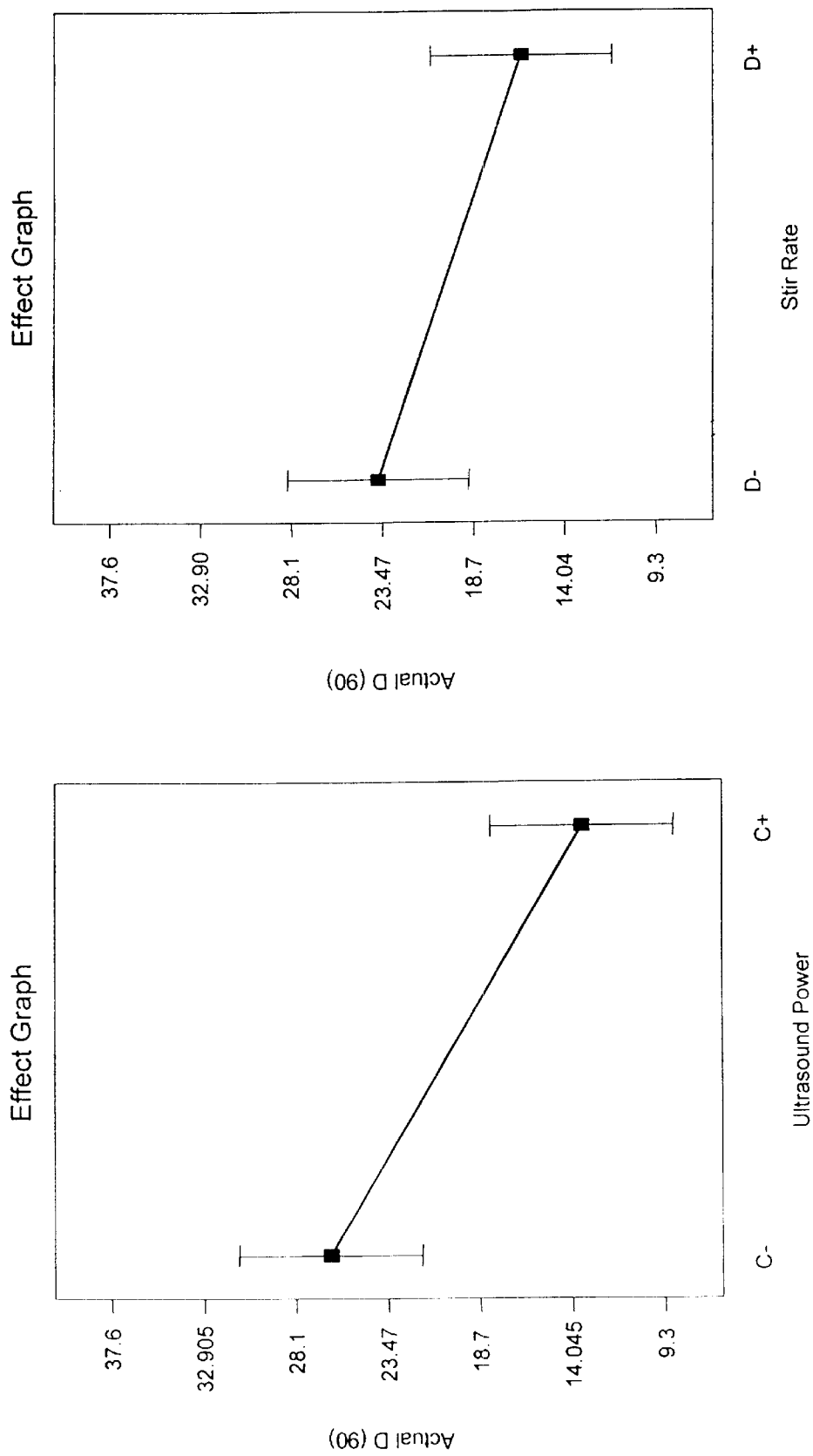

FIG. 5: effect of ultrasound power or stir rate on D90; Ultrasound has a major effect and Stirring rate has a minor effect ($R^2=0.72$).

Figure 6:
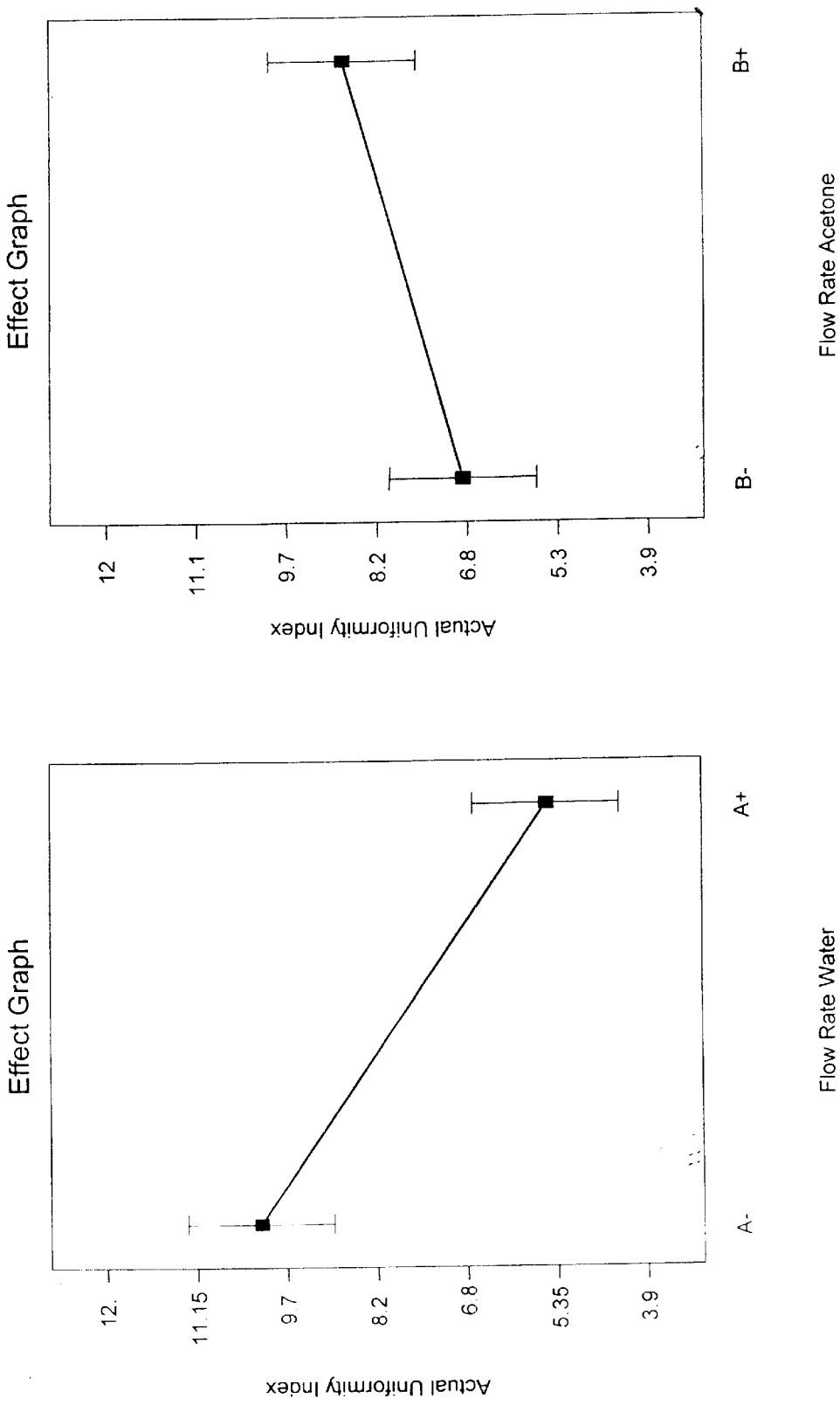

FIG. 6: effect of anti-solvent flow rate and solvent/drug solution flow rate on Ul; flow rate of anti-solvent had a major effect and flow rate of solvent/drug solution had a minor effect ($R^2=0.87$).

EXAMPLE 2

Distributions of Particles of Crystalline Salmeterol Xinafoate

Experimental Procedure

A continuous flow reaction cell with 2 diametrically opposite inlets at the bottom and a run-out ca. half way up the side of the vessel is used in the experiment. Due to the low solubility of salmeterol xinafoate and hence its propensity to crystallise from solution on cooling, a reservoir containing just pure methanol is heated to reflux and pumped through the system using a peristaltic pump so as to 'warm-up' the lines and associated apparatus. The drug substance (salmeterol xinafoate) is dissolved in methanol (6 vol) at elevated temperature (65° C.). A solution of salmeterol xinafoate (0.276 M) is then pumped (a fixed rate of 7 ml/min) using a peristaltic pump into one of the bottom inlets of the reaction cell. Cold water was similarly pumped via the other inlet from a water reservoir using a second pump at rates as dictated by the experimental design.

Re-crystallisations are carried out from various mixtures of methanol and water as dictated by the parameters set out in the experimental design. Efficient mixing of the two streams is ensured with the aid of a non-grinding magnetic stirrer bar. The stirrer speed is maintained constant at all times. The stir speed is set at such a rate so as to induce a minimum amount of vortex.

Before carrying out any particular crystallisation, the cell is pre-charged with a mixture of methanol/water (the ratio of each being the same as the relative pumping rates from the two reservoirs). By doing this, the relative concentrations of the water to methanol remains constant throughout the crystallisation. The tip of the sono-probe is arranged so that it is just above the inlet for the salmeterol solution. When the magnetic stirrer, sono-probe and pumps are turned on, rapid onset of crystallisation takes place. A suspension of the crystallisation mixture exits via the overflow directly on to a filter funnel thus minimising the opportunity for further crystal growth.

Using the above set-up, the experiments set out in the experimental design shown below were carried out and the samples of damp solid harvested and dried in vacuo at ambient temperature. All the samples were sized using the Malvern laser diffraction particle sizer and the results analysed using multi-dimensional model fitting software (such as Design Expert 5).

Experimental Design

Ultrasound and flow rate of the water were included as variables in the experimental design. Appropriate maximum and minimum values for each of the two variables were chosen as shown in Table 1.

TABLE 1

| Variable | Units | Minimum Value | Mid Point | Maximum Value |
|---|---|---|---|---|
| A Water antisolvent flow rate | ml/min | 14 | 35 | 56 |
| B Ultrasound Power | % | 10 | 50 | 90 |

A half factorial design was chosen to model the 2 variable experiment and the software package Design Expert 5 was used to generate the design.

Ultrasound Power is given as a percentage of maximum (600 W). Ultrasound frequency was 22 kHz.

Analysis

Samples were analysed using Malvern laser diffraction particle sizing.

Instrument: Malvern Mastersizer S

Lens: 300 mm Reverse Fourier

Analysis: presentation code 30 GE

Dispersant: Iso Octane / Lecithin 0.05% w/w

Pre dispersion: Sonicate for 1 Minute

Obscuration: 10% to 20%

One analysis per sample was carried out. The median particle size (D50), particle size at 90% undersize (D90) and particle size at 10 % undersize (D10) were used as responses to characterise the medium, course, and fine particles. In addition a fourth response, uniformity index (Ul) was calculated as a measure of the breadth of the distribution.

Results (a) Size Results

TABLE 2

| Run N° | Water ml/min | U/sound % | D50 (μm) | D10 (μm) | D90 (μm) | UI (%) |
|---|---|---|---|---|---|---|
| 1 | 14 | 10.00 | 10.1 | 1.6 | 24.78 | 6.46 |
| 2 | 56 | 10.00 | 3.9 | 0.48 | 10.21 | 4.70 |
| 3 | 56 | 90.00 | 4.24 | 0.64 | 14.45 | 4.42 |
| 4 | 56 | 90.00 | 4.29 | 0.53 | 17.62 | 3.01 |
| 5 | 56 | 10.00 | 4.74 | 0.39 | 16.8 | 2.32 |
| 6 | 14 | 10.00 | 11.09 | 2.17 | 23.37 | 9.28 |
| 7 | 35 | 50.00 | 4.75 | 1.08 | 13.45 | 8.03 |
| 8 | 14 | 90.00 | 6.37 | 1.63 | 20.37 | 8.00 |
| 9 | 35 | 50.00 | 4.99 | 1.88 | 11.76 | 15.99 |
| 10 | 14 | 90.00 | 7.86 | 1.77 | 24.96 | 7.09 |

Uniformity Index (UI) is calculated as 100×D 10/D90.

Figure 7:
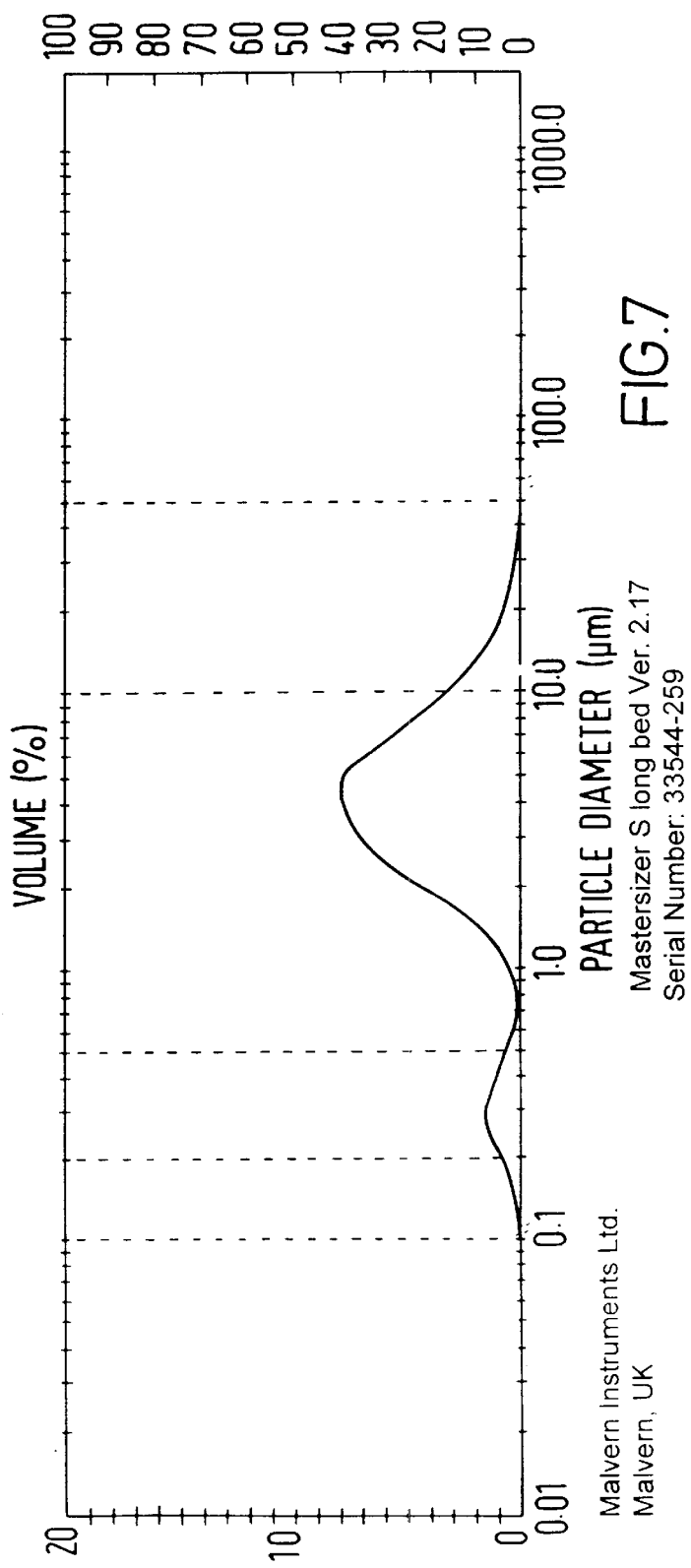

The particle size distribution for Run 2 is shown graphically in FIG. 7.

Figure 8:
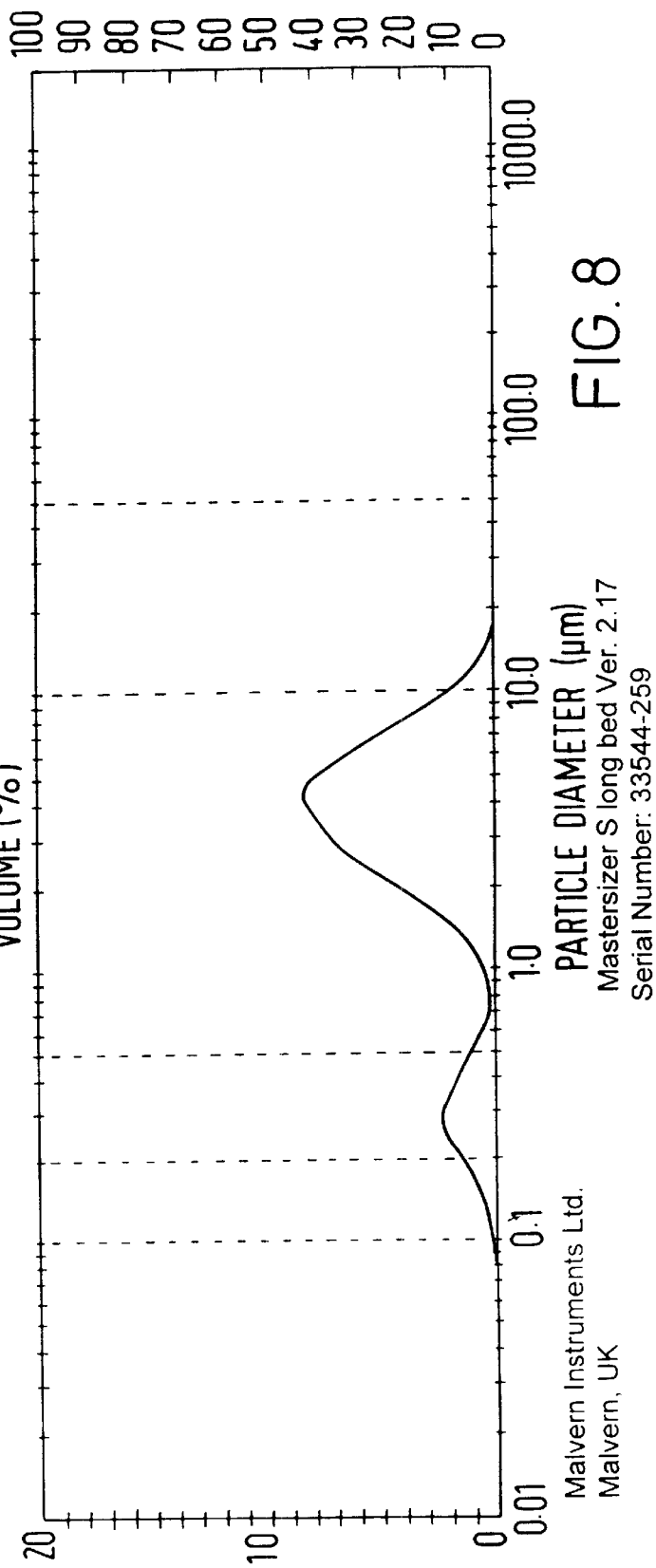

The distribution of a standard micronised batch of salmeterol xinafoate is shown for comparison in FIG. 8.

(b) Analysis of effects

Figure 9:
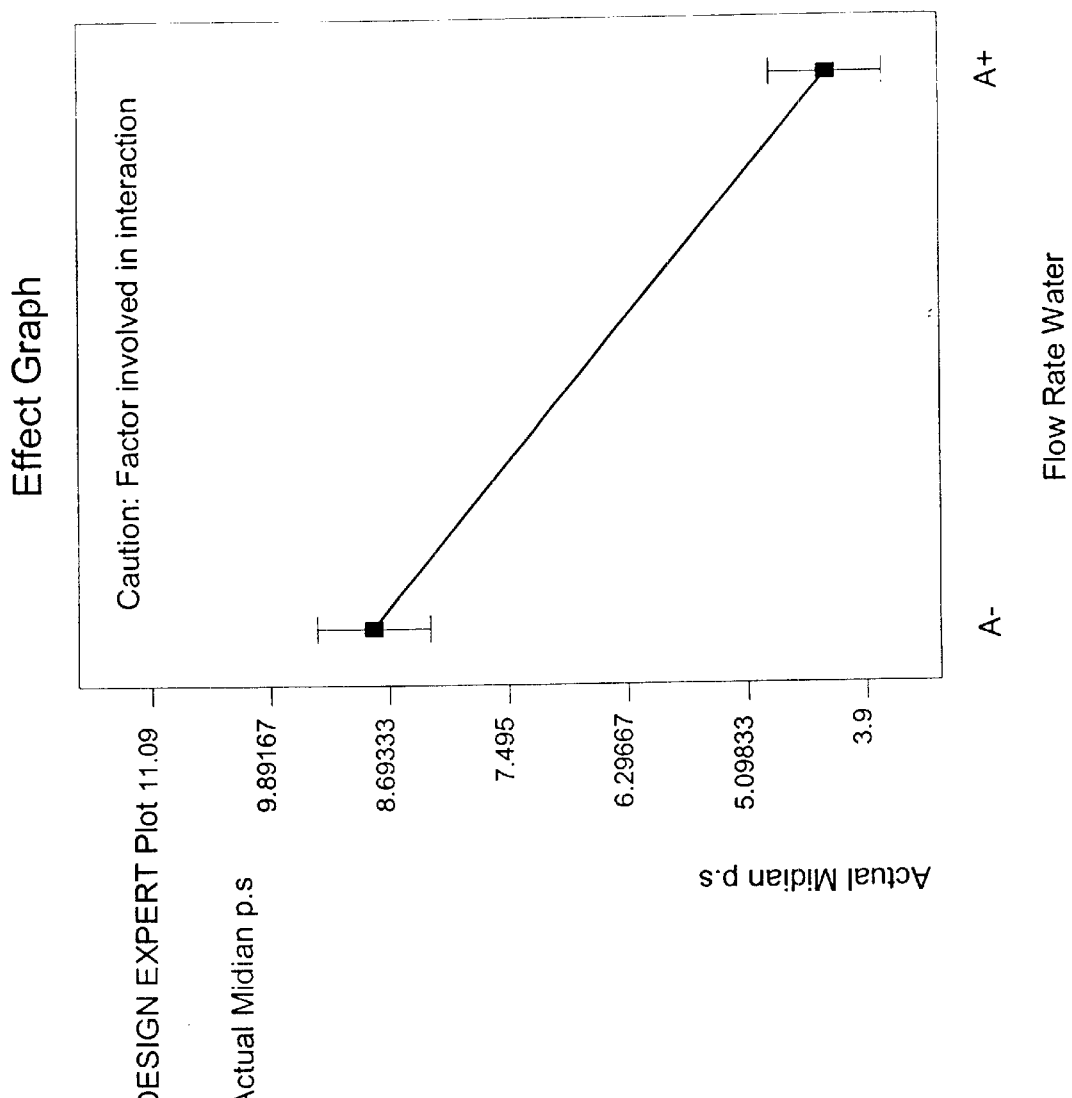
Figure 10:
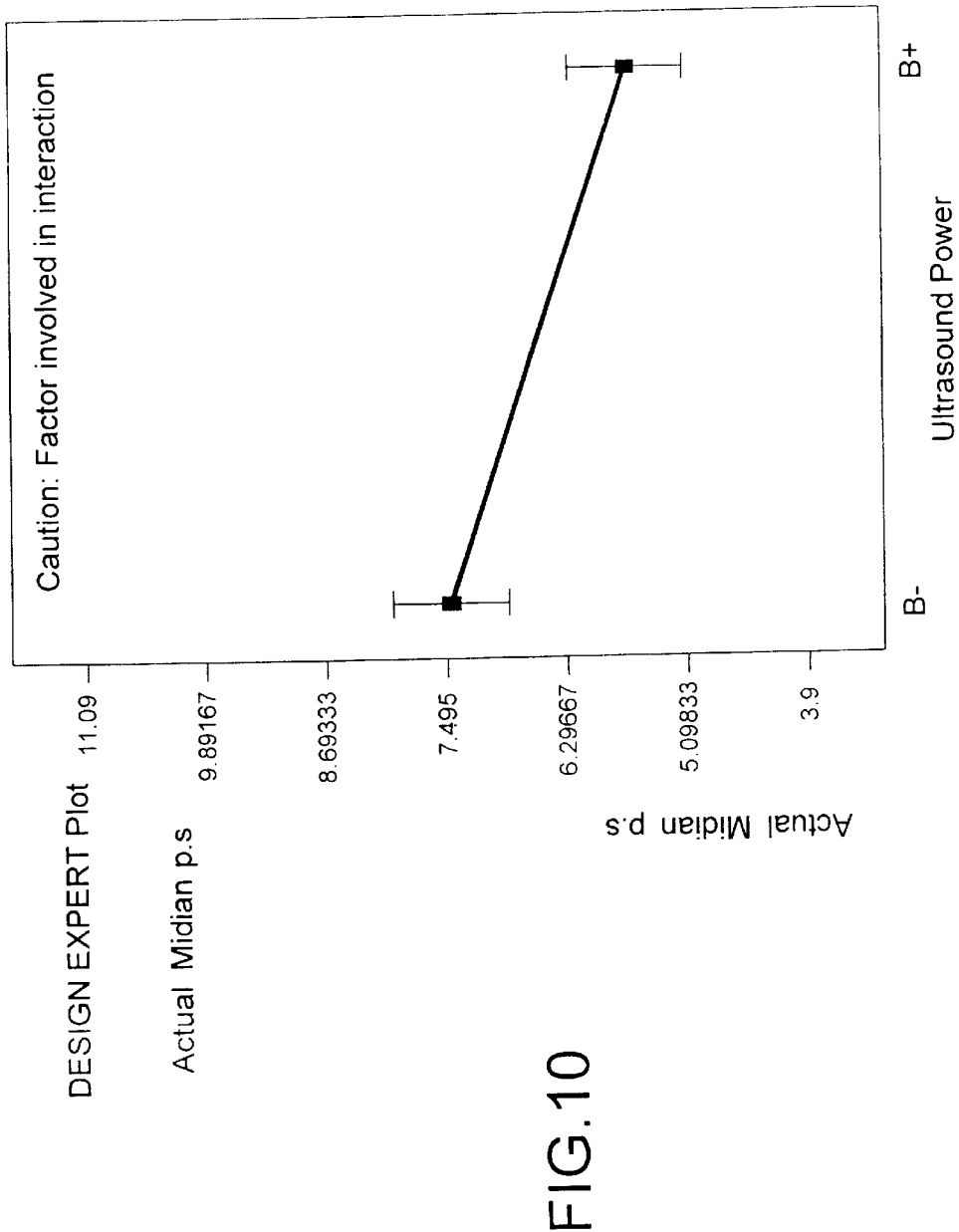

Effect graphs to show the interdependence of pairs of variables A and B were constructed using Design Expert 5 and are shown in FIGS. 9–10.

FIG. 9: effect of water anti-anti-solvent flow rate on D50; water anti-solvent flow rate has a major effect.

FIG. 10: effect of ultrasound power on D50; ultrasound power has a minor effect.

EXAMPLE 3

An aluminium canister may be charged with particles of (a) fluticasone propionate or (b) salmeterol xinafoate prepared according to the invention. A metering valve (Valois) may be crimped on and liquefied HFA134a added through the valve.

EXAMPLE 4

A dry powder composition for inhalation may be prepared by mixing particles of (a) fluticasone propionate or (b) salmeterol xinafoate prepared according to the invention with milled lactose.

What is claimed is:

1. A process for preparing crystalline particles of substance which comprises mixing in a continuous flow cell in the presence of ultrasonic radiation a flowing solution of the substance in a liquid solvent with a flowing liquid antisolvent for said substance which is miscible with the liquid solvent, and collecting the resultant crystalline particles generated.

2. An apparatus for preparing crystalline particles of a substance which comprises (i) a first reservoir of said substance dissolved in a liquid solvent;

(ii) a second reservoir of liquid antisolvent for said substance which is miscible with the liquid solvent;

(iii) a mixing chamber having first and second inlet ports and an outlet port;

(iv) means for delivering the contents of the first and second reservoirs to the mixing chamber via the first and second inlet ports respectively at independent controlled flow rate;

(v) a source of ultrasonic radiation located in the vicinity of the first inlet; and (vi) means for collecting particles suspended in the liquid discharged from the mixing chamber at the outlet port.

3. An apparatus according to claim 2 further comprising means to mix the liquids delivered to the mixing chamber via the first and second inlets.

4. An apparatus according to claim 3 wherein the mixing means comprises a stirrer.

5. An apparatus according to claim 2 wherein the means for delivering the contents of the first and second reservoirs to the mixing chamber via the first and second inlet ports respectively at independent controlled flow rate comprises one or more pumps.

6. An apparatus according to claim 2 wherein the outlet port is disposed above the inlet ports in the mixing chamber such that the liquid in the mixing chamber flows from a lower to a higher point in the chamber before exiting.

7. An apparatus according to claim 2 wherein the mixing chamber is substantially circular in section and the first and second inlet ports are disposed diametrically opposite each other and at the same height relative to the base of the mixing chamber.

8. An apparatus according to claim 2 wherein the means for collecting particles suspended in the liquid discharged from the mixing chamber at the outlet port comprises a filter.

9. A process for preparing crystalline particles of substance which comprises mixing in a continuous flow cell in the presence of ultrasonic radiation a flowing solution of the substance in a liquid solvent with a flowing liquid antisolvent for said substance which is miscible with the liquid solvent, and collecting the resultant crystalline particles generated, which process comprises the steps of:

(a) providing an apparatus for preparing crystalline particles of a substance which comprises (i) a first reservoir of said substance dissolved in a liquid solvent;

(ii) a second reservoir of liquid antisolvent for said substance which is miscible with the liquid solvent;

(iii) a mixing chamber having first and second inlet ports and an outlet port;

(iv) means for delivering the contents of the first and second reservoirs to the mixing chamber via the first and second inlet ports respectively at independent controlled flow rate;

(v) a source of ultrasonic radiation located in the vicinity of the first inlet; and (vi) means for collecting particles suspended in the liquid discharged from the mixing chamber at the outlet port, (b) delivering the contents of the first and second reservoirs to the mixing chamber via the first and second inlet ports respectively at independent controlled flow rate;

(c) supplying ultrasonic radiation to the vicinity of the first inlet; and (d) collecting the crystalline particles suspended in the liquid discharged from the mixing chamber at the outlet port.

10. A process according to claim 9 wherein the substance is a pharmaceutical or carrier substance suitable for inhalation therapy.

11. A process according to claim 10 wherein the substance is fluticasone, beclomethasone, salmeterol, salbutamol or an ester, salt or solvate thereof.

12. A process according to claim 10 wherein the substance is lactose.

13. A process according to claim 11 wherein the substance is fluticasone propionate.

14. A process according to claim 13 wherein the solvent is acetone and the anti-solvent is water.

15. A population of particles obtainable by a process according to claim 1.

16. A population of particles obtainable by a process according to claim 9.

17. A pharmaceutical composition comprising a population of particles according to claim 15.

18. A pharmaceutical composition comprising a population of particles according to claim 16.

* * * * *